US012629224B2

(12) United States Patent
Kim et al.

(10) Patent No.: US 12,629,224 B2
(45) Date of Patent: May 19, 2026

(54) HEADSET-BASED VISION DEVICE FOR TRANSMITTING MULTIPLE MEDICAL IMAGES AND PROVIDING SURGICAL ASSIST FUNCTION

(71) Applicants: Seoul National University Hospital, Seoul (KR); Seoul National University R&DB Foundation, Seoul (KR)

(72) Inventors: Sungwan Kim, Yongin-si (KR); Minwoo Cho, Seoul (KR); Jonghyeon Lee, Chuncheon-si (KR); Young Gyun Kim, Busan (KR); Byeong Soo Kim, Seoul (KR); Dan Yoon, Seoul (KR)

(73) Assignees: Seoul National University Hospital, Seoul (KR); Seoul National University R&DB Foundation, Seoul (KR)

( * ) Notice: Subject to any disclaimer, the term of this patent is extended or adjusted under 35 U.S.C. 154(b) by 378 days.

(21) Appl. No.: 18/110,825

(22) Filed: Feb. 16, 2023

(65) Prior Publication Data

US 2024/0074827 A1    Mar. 7, 2024

(30) Foreign Application Priority Data

Sep. 5, 2022    (KR) ........................ 10-2022-0112386

(51) Int. Cl.
*G06F 3/048* (2013.01)
*A61B 34/37* (2016.01)
(Continued)

(52) U.S. Cl.
CPC .............. *A61B 34/37* (2016.02); *A61B 90/37* (2016.02); *G06T 19/00* (2013.01); *H04N 13/117* (2018.05);
(Continued)

(58) Field of Classification Search
CPC ... A61B 34/37; A61B 90/37; A61B 2090/372; H04N 13/383; H04N 13/117; H04N 13/344; G06T 2210/41; G06T 16/00
See application file for complete search history.

(56) References Cited

U.S. PATENT DOCUMENTS 6,847,336 B1 *   1/2005   Lemelson .............. H04N 7/147
                                                           345/8
9,814,536 B2 *   11/2017  Goldberg ............... A61B 34/37
                          (Continued)

FOREIGN PATENT DOCUMENTS

KR       20210048954 A  *  5/2021  ............. A61B 90/39

*Primary Examiner* — Linh K Pham
(74) *Attorney, Agent, or Firm* — Park, Kim & Suh, LLC

(57) ABSTRACT

A headset of a surgical robot system includes an endoscope image transmission module configured to transmit an endoscope image to a main screen, a surgical assist function transmission module configured to transmit a selected and activated surgical assist function on an auxiliary screen positioned at one side of the main screen, a surgical assist function optional transmission module configured to transmit a list of a plurality of surgical assist functions to be provided on the auxiliary screen to a selection screen, an acceleration sensor and a gyroscope, configured to detect a change in a position of a head of a user, an eye tracking module configured to detect a change in a user gaze and a change in focus, and a controller configured to control a specific surgical assist function selected from among the plurality of surgical assist functions to be provided to the auxiliary screen.

10 Claims, 8 Drawing Sheets

(51) Int. Cl.

| | |
|---|---|
| *A61B 90/00* | (2016.01) |
| *G06T 19/00* | (2011.01) |
| *H04N 13/117* | (2018.01) |
| *H04N 13/344* | (2018.01) |
| *H04N 13/383* | (2018.01) |

(52) U.S. Cl.

CPC ......... *H04N 13/344* (2018.05); *H04N 13/383* (2018.05); *A61B 2090/372* (2016.02); *G06T 2210/41* (2013.01)

(56) References Cited

U.S. PATENT DOCUMENTS

| | | | | |
|---|---|---|---|---|
| 9,844,321 | B1 * | 12/2017 | Ekvall .................. | A61B 3/0025 |
| 11,931,119 | B1 * | 3/2024 | Levin ..................... | A61B 34/25 |
| 2008/0120141 | A1 * | 5/2008 | Kariathungal .......... | G06F 3/013 |
| | | | | 705/3 |
| 2009/0036902 | A1 * | 2/2009 | DiMaio ................... | A61B 8/12 |
| | | | | 606/130 |
| 2013/0172906 | A1 * | 7/2013 | Olson .................... | A61B 34/30 |
| | | | | 606/130 |
| 2016/0225192 | A1 * | 8/2016 | Jones ..................... | G06F 3/017 |
| 2017/0020431 | A1 * | 1/2017 | Flitsch .................. | A61B 5/1118 |
| 2017/0172675 | A1 * | 6/2017 | Jarc ........................ | A61B 34/35 |
| 2018/0177558 | A1 * | 6/2018 | McKinley .............. | A61B 34/00 |
| 2019/0099226 | A1 * | 4/2019 | Hallen ..................... | A61B 3/13 |
| 2019/0328470 | A1 * | 10/2019 | Tojo ...................... | A61B 34/25 |
| 2019/0328472 | A1 * | 10/2019 | Tojo ................... | A61B 17/3423 |
| 2020/0038120 | A1 * | 2/2020 | Ziraknejad ............. | A61B 34/25 |
| 2020/0237452 | A1 * | 7/2020 | Wolf ....................... | G06F 3/048 |
| 2020/0375666 | A1 * | 12/2020 | Murphy ................ | G06T 19/006 |
| 2020/0405420 | A1 * | 12/2020 | Purohit ................. | A61B 34/20 |
| 2021/0022599 | A1 * | 1/2021 | Freeman .............. | A61B 3/0025 |
| 2021/0065746 | A1 * | 3/2021 | Sugano ................ | G11B 27/031 |
| 2021/0169578 | A1 * | 6/2021 | Calloway ........... | G02B 27/0172 |
| 2021/0315662 | A1 * | 10/2021 | Freeman ................ | G06F 3/012 |
| 2021/0335483 | A1 * | 10/2021 | Freeman ................ | G16H 50/20 |
| 2021/0382559 | A1 * | 12/2021 | Segev ................. | G06V 10/806 |
| 2021/0386503 | A1 * | 12/2021 | Healy ................... | G16H 50/20 |
| 2021/0401527 | A1 * | 12/2021 | Hassan ................. | A61B 34/30 |
| 2022/0022982 | A1 * | 1/2022 | Hares ..................... | A61B 34/30 |
| 2022/0104910 | A1 * | 4/2022 | Shelton, IV .......... | G16H 40/63 |
| 2022/0110682 | A1 * | 4/2022 | Tseng ..................... | G06T 19/20 |
| 2022/0387128 | A1 * | 12/2022 | Bail ....................... | A61B 90/36 |
| 2023/0014033 | A1 * | 1/2023 | Tojo ....................... | A61B 17/34 |
| 2024/0024030 | A1 * | 1/2024 | Kenny .................. | A61B 34/25 |
| 2024/0268628 | A1 * | 8/2024 | Katsuki ................ | G16H 40/67 |
| 2024/0423724 | A1 * | 12/2024 | Wolf ...................... | A61B 34/10 |

* cited by examiner

ACTIVATE SURGICAL ASSIST FUNCTION — S10

SELECT SURGICAL ASSIST FUNCTION — S20

ENTER SELECTION STATE — S30

SELECT AUXILIARY SCREEN — S40

COMPLETE ACTIVATION — S50

ANOTHER FUNCTION ACTIVATED? — S70

YES

NO

RETURN TO NORMAL STATE — S60

12          11(13)

HEADSET-BASED VISION DEVICE FOR TRANSMITTING MULTIPLE MEDICAL IMAGES AND PROVIDING SURGICAL ASSIST FUNCTION

CROSS-REFERENCE TO RELATED APPLICATIONS

This application claims the benefit of Korean Patent Application No. 10-2022-0112386, filed on Sep. 5, 2022, which is hereby incorporated by reference as if fully set forth herein.

BACKGROUND

Technical Field

The present disclosure relates to a surgical robot system for minimally invasive surgery and a control method thereof, and more particularly to a surgical robot system using a vision headset and a control method thereof.

The present disclosure relates to a headset-based vision device to be applied to a surgical robot system and a control method thereof.

Discussion of the Related Art

Minimally invasive surgery using a surgical robot is a technique for performing surgery by making minimal incisions on a patient, and contributes to improving prognosis of the patient with various advantages (minimization of blood loss, rapid recovery, shortened hospitalization period, etc.) compared to open surgery.

The da Vinci Surgical System (dVSS) surgical robot from Intuitive Surgical Inc. as the most widely used surgical robot at home and abroad is broadly configured by a surgeon console operated by an operating surgeon and a patient cart located at a patient side.

The surgeon console is configured by a stereo viewer that is a vision device for transmitting a real-time 3D image to the operating surgeon, a master tool manipulator (MTM) for manipulating the position of the robot, and a foot pedal tray for performing various special functions.

The patient cart includes manipulators for mounting a surgical tool and an endoscope camera thereon. Depending on functions provided, the manipulator is classified into apatient side manipulator (PSM), which mounts a surgical tool thereon for applying direct manipulation to the patient, and an endoscopic camera manipulator (ECM), which mounts an endoscope camera thereon for providing a surgical view to the operating surgeon.

The MTM is a device for controlling the positions of the PSM and the ECM, and the operating surgeon operates the MTM by using movements of the hand and the wrist within an allowable operating range. The corresponding movement is reflected in the movement of the manipulator of the patient cart and the mounted surgical tool, which the operating surgeon has control over.

The foot pedal tray includes pedals that acquire control over an operation of each manipulator located in the patient cart, such as a switch, clutch, and camera, and perform various functions. The switch pedal allows the operating surgeon to acquire control over the manipulator to be used. The clutch pedal repositions the MTM and hands of the operating surgeon while the manipulator does not move. Thus, the operating surgeon may smoothly perform surgery within a limited range of an operation of the MTM. When a camera pedal is depressed, it is possible to acquire control over the position of the ECM, and thus the position of the endoscope camera may be moved.

The stereo viewer transmits an image taken at different viewpoints to each eye of the operating surgeon to artificially feel parallax to allow the operating surgeon to feel a sense of depth and immersion.

However, the vision device of the surgical robot is very bulky and has a limitation in that a surgical space is inefficiently utilized. In addition, currently used surgical robots need to fix their gaze inside the vision device throughout the surgical procedure. The operating surgeon sits in a fixed posture and uses his or her hands to perform the operation, with a field of view facing the inside of the vision device. In this case, the conventional vision device does not reflect ergonomic characteristics well, and physical fatigue is accumulated, which acts as a cause of chronic joint pain and discomfort. In addition, an image transmitted to the vision device of the surgical robot is limited to a field of view related to a surgical scene, and thus in order to check medical information about the patient, such as vital signs, it is necessary to take the operating surgeon's gaze off the existing vision device and check the information. Therefore, in the case of using the conventional surgical robot, there is a limitation that a flow of surgery is temporarily interrupted by stopping a surgical process, and furthermore, there is a possibility that a life-and-death operation may have a fatal effect on the patient's prognosis.

SUMMARY

An object of the present disclosure is to overcome a problem of a conventional robot surgery system and a vision device thereof.

An embodiment of the present disclosure may provide a robot surgery system for efficiently utilizing a space for surgery, and a vision device thereof.

An embodiment of the present disclosure may provide a robot surgery system for performing surgery in a more improved environment by relieving constraints of the operating surgeon on the vision device, and a vision device thereof.

An embodiment of the present disclosure may provide a robot surgery system for minimizing interruption of a flow of surgery and improving clinical convenience by providing various surgical assist functions to the operating surgeon through a headset, and a vision device thereof.

An embodiment of the present disclosure may provide a robot surgery system for easily activating and selecting a surgical assist function through a change in the gaze of the operating surgeon, and a vision device thereof.

An embodiment of the present disclosure may provide a robot surgery system for providing a customized surgery platform depending on an operating surgeon, and a vision device thereof.

An embodiment of the present disclosure may provide a vision platform and a vision device which are to be easily applied to the conventional robot surgery system.

An embodiment of the present disclosure may provide a surgical robot system including a surgeon console including a vision device configured to provide a surgical view to a user and allow the user to perform surgery manipulation, and a patient cart located at a side of a patient and configured to apply the surgery manipulation of the user through the surgeon console and perform surgery, wherein the vision device includes a headset that the user wears, and the headset includes a main display region provided to the user to distinguish between a surgical view and a surgical assist function image in a VR environment, and an auxiliary display region provided to the user to select and activate the surgical assist function by the user in the VR environment and located at one side of the main display region.

The main display region may include a main screen located in a center and configured to provide a current surgical view to the user, and a plurality of auxiliary screens located on left and right sides of the main screen and configured to provide the surgical assist function selected and activated through the auxiliary display region to the user.

The auxiliary display region may include a plurality of selection screens configured to display respective surgical assist functions.

The auxiliary display region may be located at a left or right side of the main display region. Thus, when the operating surgeon is concentrated into, in particular, the main screen, the auxiliary display region may be completely out of a view of the operating surgeon.

The headset may include an eye tracking module configured to track a change in a user gaze and a change in focus, and an acceleration sensor and a gyroscope, configured to detect movement of a head of the user wearing the headset.

A position corresponding to a depth direction of the main screen, an auxiliary screen, and a selection screen may be automatically adjusted based on a tracking result of the eye tracking module.

Selection of the user for a specific surgical assist function among the plurality of surgical assist functions and selection of the user for a specific auxiliary screen for providing the selected surgical assist function among the plurality of auxiliary screens may be performed through eye blinking of the user a predetermined number of times for a predetermined period of time.

That is, user head position detection technology based on acceleration sensor and gyroscope and eye tracking technology based on infrared rays may be applied to selection of a detailed object, for example, selection of a surgical assist function and/or a screen.

The acceleration sensor and the gyroscope may be separately provided or may be integrated into each other.

The surgical assist function may include at least one of real-time medical information of the patient, visual information of a bleeding area in a surgical view, visual information highlighting major lesions or tissues in the surgical view, reference information for a surgery guide, surgery prognostic prediction information, or information on calculation of an improvement degree and prognostic prediction of the patient during resurgery.

To achieve the above-described objects, an embodiment of the present disclosure provides a headset of a surgical robot system including an endoscope image transmission module configured to transmit an endoscope image to a main screen, a surgical assist function transmission module configured to transmit a selected and activated surgical assist function on an auxiliary screen positioned at one side of the main screen, a surgical assist function optional transmission module configured to transmit a list of a plurality of surgical assist functions to be provided on the auxiliary screen to a selection screen, an acceleration sensor and a gyroscope, configured to detect a change in a position of a head of a user, an eye tracking module configured to detect a change in a user gaze and a change in focus, and a controller configured to control a specific surgical assist function selected from among the plurality of surgical assist functions to be provided to the auxiliary screen, based on a tracking result of the eye tracking module.

The auxiliary screen may include a left auxiliary screen provided on a left side of the main screen and a right auxiliary screen provided on a right side.

The controller may control the selected specific surgical assist function to be provided to any one auxiliary screen selected from the left auxiliary screen or the right auxiliary screen.

Selection of the user for a specific surgical assist function among the plurality of surgical assist functions and selection of the user for a specific auxiliary screen for providing the selected surgical assist function among the plurality of auxiliary screens may be performed through eye blinking of the user a predetermined number of times for a predetermined period of time. Accordingly, the user may select and operate intuitively and easily without using hands or feet.

The headset may further include an alarm transmission module configured to inform the user of break recommendation. For example, the tracking result through the eye tracking module may be analyzed through an artificial intelligence module to predict fatigue of the operating surgeon and to inform the user of break recommendation.

The surgical assist function may include at least one of real-time medical information of the patient, visual information of a bleeding area in a surgical view, visual information highlighting major lesions or tissues in the surgical view, reference information for a surgery guide, surgery prognostic prediction information, or information on calculation of an improvement degree and prognostic prediction of the patient during resurgery.

The controller may automatically adjust a position corresponding to a depth direction of the main screen, an auxiliary screen, and a selection screen based on a tracking result of the eye tracking module.

The headset may further include an input and output module configured to transmit and receive data to and from a peripheral device of the surgical robot system.

DETAILED DESCRIPTION

Figure 1:
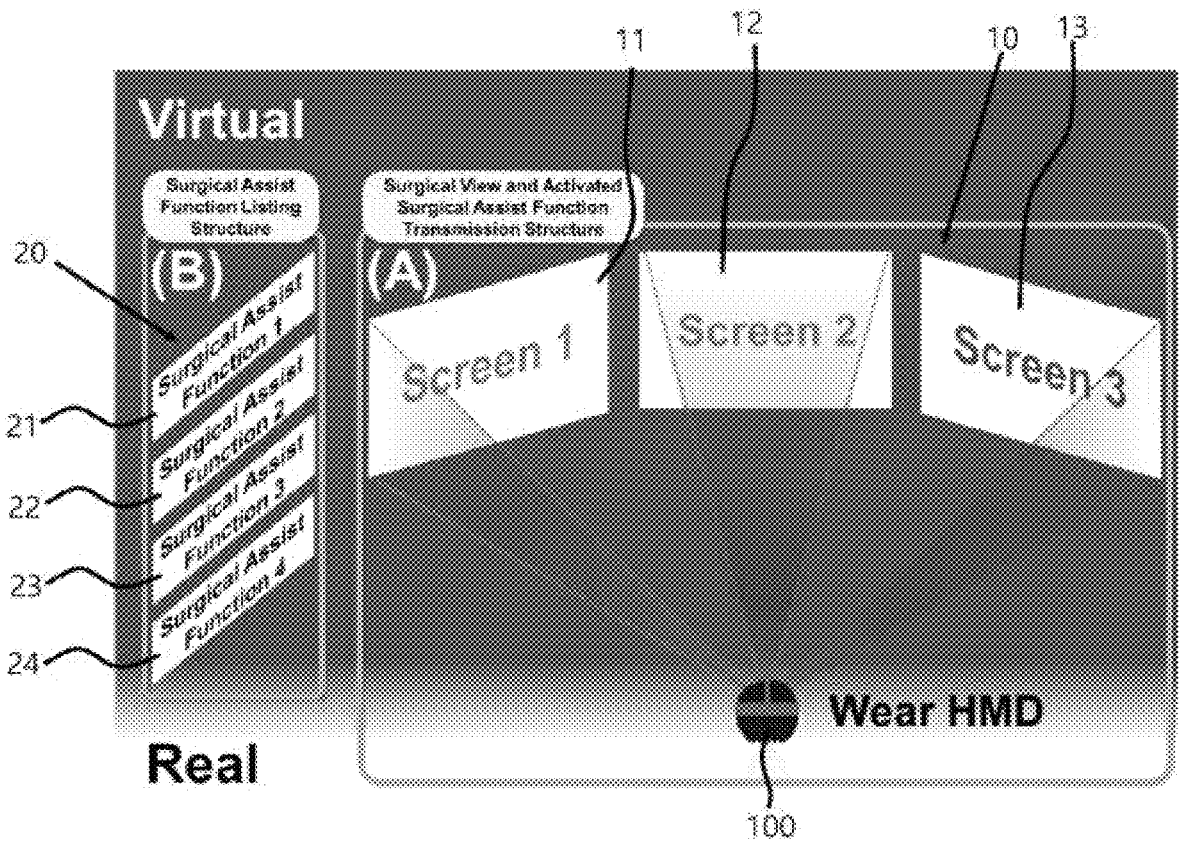
FIG. 1 is a schematic diagram showing a concept of a display provided to a user in a VR environment after the user wears a headset.

According to one embodiment of the present disclosure, a vision device of a conventional surgical robot may be replaced with a VR headset. In particular, provided are a surgical robot including a headset for implementing not only virtual reality but also mixed reality (MR), and a control method thereof.

Here, a headset means a head mounted display (HMD) and may be referred to as a monitor worn and used by a user like glasses. Recently, it is also called a face mounted display (FMD).

Mixed reality (MR) is a concept that covers a series of spectrums between reality and virtual reality (virtuality), and representative examples include augmented reality (AR), which overlays a virtual element on a real environment, and an augmented virtuality (AV), which adds an element of reality to a virtual environment. Mixed reality provides a user with a three-dimensional and realistic 3D image, and virtual reality headsets that are to be worn on the head and transmit different images in front of each eye are widely used. According thereto, it may be possible to build a wide-angle virtual environment by establishing a reference coordinate system of the headset in real time depending on an angle of rotation (flexion, extension, rotation, etc.) of the neck of the operating surgeon based on a gyroscope as an angular velocity sensor for tracking a relative position of the headset in real time based on an infrared signal transmitted from multiple fixed base stations and recognizing changes in direction and position inherent in the headset. In addition, the operating surgeon may interact with a mixed reality interface through various inputs (controller, changes in position and posture of headset, voice, etc.) and output (sound, vibration, screen, etc.) channels. In addition, the virtual reality headset has a built-in camera on a front and side of the headset to acquire a view of surroundings of the operating surgeon and is used as another input channel.

According to an embodiment of the present disclosure, eye tracking technology may be applied.

A gesture-based interface used as an input and control device in immersive technologies such as mixed reality is created by physical actions such as user hand and body movements, eye blinking, and head movements. In this case, sight is the most sensitive and responsive sensory organ among the five senses, and eye tracking technology is one of the most effective element for interaction between users and information devices. Therefore, the eye tracking technology may be applied as a gesture-based interface of the headset implementing mixed reality.

Eye tracking technology is a technology that detects the movement of the pupil and tracks the position of the gaze, and eye movements are stored as data in a computer according to a principle that infrared rays are injected into the cornea on a surface of the eye and the camera recognizes and tracks the infrared rays reflected from the cornea. When measuring the eye movements, it may be possible to simultaneously record information on the position and time of a viewpoint and classify the eye movements using the corresponding data. Eye tracking technology may be broadly classified into remote eye tracking device (RED) and head-mounted eye tracking device (HED) methods.

The RED refers to a method of automatically measuring movement of the gaze without direct contact with the eyes, and poses a difficulty in that a subject is not capable of moving the body freely when measuring a focus of the eye and needs to maintain the position of the head in a fixed posture. However, with the HED, the subject wears a separate headset with a camera attached thereto and allows spatial exploration while freely moving the body. Accordingly, the HED may investigate movement of the eyes according to dynamic movement and has the characteristics of being able to experiment with a three-dimensional object.

Therefore, the eye tracking technology using the HED method may be applied as a gesture-based interface of a headset for implementing mixed reality.

Accordingly, the present disclosure relates to a vision device including a headset for implementing mixed reality to which eye tracking technology is applied as described above in order to overcome the problems of the vision device of a conventional surgical robot.

That is, according to an embodiment of the present disclosure, virtual reality technology is applied to replace the existing surgical robot vision device, and a vision device and a platform may be provided to transmit a surgical view and a surgical assist function, which provides convenience as well as medical information of a patient, in virtual reality.

Hereinafter, a vision device according to an embodiment of the present disclosure will be described in detail with reference to the accompanying drawings.

FIG. 1 is a schematic diagram showing a concept of a display provided to a user in a VR environment after the user wears a headset.

As shown in the drawing, a display in the headset may include a main display 10 and an auxiliary display 20. A region (A) may be the main display 10, and a region (B) may be an auxiliary display 20.

The main display 10 may include a plurality of screens 11, 12, and 13, and the auxiliary display 20 may also include a plurality of selection screens 21, 22, 23, and 24. Needless to say, the numbers of the respective screens may be changed.

The user may perform surgery after wearing the headset. For example, when endoscope surgery is performed, the user may perform the surgery while watching an endoscope image. Therefore, the endoscope image may be transmitted and displayed on the main display 10. In particular, since the user may perform the surgery while gazing at the front, an endoscope image may be displayed on a central screen 12.

The user may refer to various types of auxiliary information while performing surgery. That is, the headset may be made to perform an assist function of displaying auxiliary information rather than simply performing a function of displaying a basic endoscope image. In other words, an assist function of displaying information that the user is capable of referring to during surgery may be added.

Thus, the main display 10 may include auxiliary screens 11 and 13 for displaying the assist function. The auxiliary screens 11 and 13 may be provided on the left or right side of the central screen 12, and the user may easily recognize auxiliary information by moving the gaze to the left or right while viewing the central screen 12 and performing surgery.

For example, auxiliary screens may be provided on the left and right sides of the central screen 12, that is, the main screen, respectively. For convenience, the auxiliary screen 11 at the left side may be referred to as the left auxiliary screen 11, and the auxiliary screen 13 at the right side may be referred to as the right auxiliary screen 13.

The user may turn the head left and right instead of moving the gaze. That is, the user may stare at the auxiliary screen 11 while turning the head to the left, and gaze at the auxiliary screen 13 while turning the head to the right. Then, after checking the auxiliary information, the user may perform surgery while watching the central screen after turning the head forward. Here, different types of surgical auxiliary information may be provided to the left auxiliary screen 11 and the right auxiliary screen 13. Therefore, it may be possible to check the surgical auxiliary information very simply and easily.

In other words, the main display 10 may be divided into a part 12 in which an endoscope image for a surgical view is transmitted and parts 11 and 13 in which a surgical assist function is visually transmitted.

Surgical assist functions may be very diverse, and in particular, necessary surgical assist functions may vary according to a progress of surgery. However, due to a limited space of the main display 10, it may not be easy to simultaneously display various surgical assist functions. For example, the size of the central screen 12 in which endoscope images are transmitted may be reduced and the number of auxiliary screens may be increased. Therefore, the assist function transmitted from the main display 10 may be selected by the user.

For example, only the assist function activated by user selection may be transmitted and displayed on the auxiliary screens 11 and 13.

The auxiliary display 20 may be provided on one side of the main display 10, and may be provided on the left or right side out of a field of view of the user when the user gazes at the front. For example, the auxiliary display 20 may be provided to the left of the main display 10.

The plurality of selection screens 21, 22, 23, and 24 may be arranged on the auxiliary display 20, and a corresponding assist function may be displayed in characters or the like on each of the selection screens. Needless to say, when there are more assist functions, the number of selection screens may be larger. That is, the auxiliary display 20 may be a part for listing surgical assist functions to be activated. FIG. 1 shows an example in which four surgical assist functions are listed.

Accordingly, the user may select a necessary surgical assist function to be activated through the auxiliary display 20 as the surgery is performed, and the selected and activated surgical assist function may be viewed through the main display 10. In other words, optimal surgery may be performed by utilizing not only the endoscope image but also the currently necessary surgical assist function.

Robot surgery may be applied to various parts such as the gallbladder, appendix, thyroid gland, and stomach/colon, and there may be various types of surgery depending on the part. Depending on the surgical site and type, the medical information that the operating surgeon needs to intensively check and refer to and the type of surgical assist function to be usefully utilized may be different. Accordingly, the history of the surgical assist function previously used by the operating surgeon and the auxiliary screen that transmits the function may be recorded according to the surgical site and type. Then, the corresponding information may be analyzed based on an artificial intelligence algorithm, and a surgical assist function and an auxiliary screen to transmit the corresponding function may be recommended when surgery on the same surgical site and type is performed in the future. This makes it possible to recommend an effective surgical assist function and auxiliary screen as surgical data accumulates, and may contribute to improving the convenience of the user (operating surgeon).

Finally, surgical assist functions to be selected may be listed on the selection screens provided on the auxiliary display 20, and there through, the currently displayed surgical assist function may be changed to another assist function.

Figure 2:
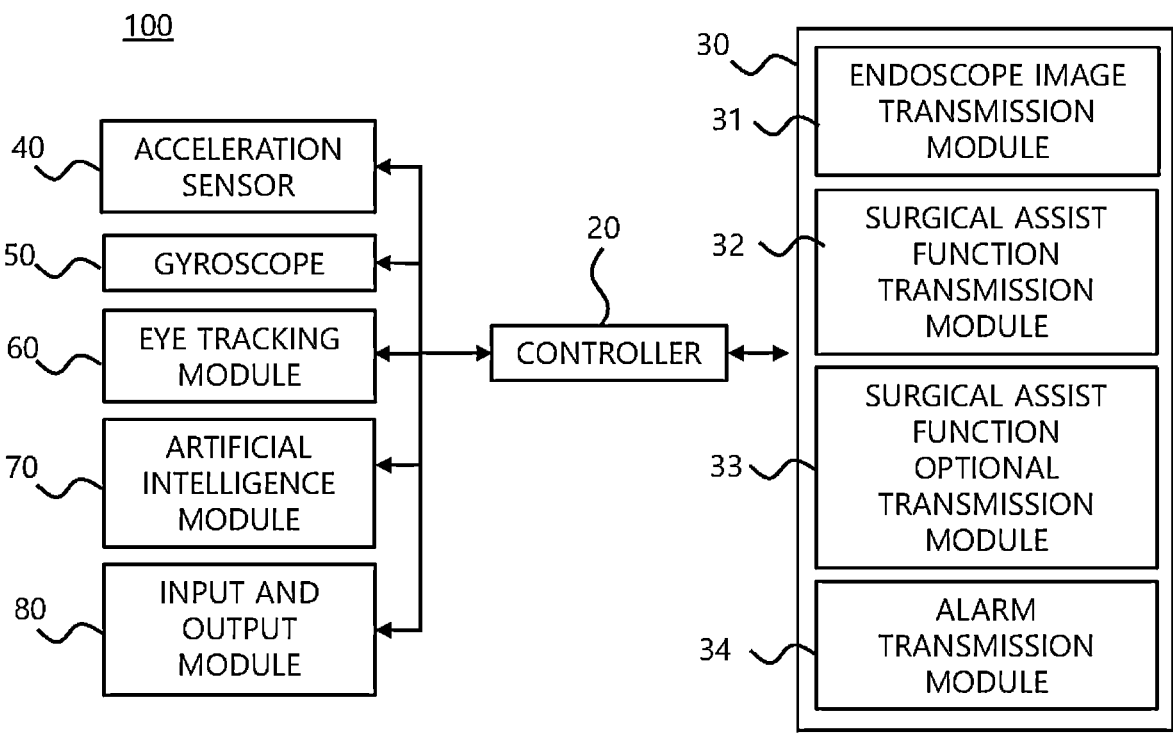
FIG. 2 shows a control configuration of a headset according to an embodiment of the present disclosure.

Hereinafter, a control configuration of a headset according to an embodiment of the present disclosure will be described in detail with reference to FIG. 2.

A headset 100 may include an image transmission module 30. The image transmission module 30 may transmit and display images or information input through an input and output module 80.

The image transmission module 30 may include an endoscope image transmission module 31, through which an image obtained through a camera currently installed in the endoscope may be transmitted to the main screen 12.

The image transmission module 30 may include a surgical assist function transmission module 32. Through this, the surgical assist function selected and activated on each of the auxiliary screens 11 and 13 may be transmitted.

The image transmission module 30 may include a surgical assist function optional transmission module 33 for transmitting a selectable surgical assist function. Through this, the name or information of the surgical assist function to be selected on each of the selection screens 21, 22, 23, and 24 may be transmitted.

The image transmission module 30 may include an alarm transmission module 34. The alarm means information for arousing attention of the operating surgeon, and may be, for example, a break recommendation message. Alarm information may be displayed on an upper or lower side of the main screen 12. That is, the operating surgeon may easily recognize the alarm information while watching the main screen 12 without moving the head during surgery.

The image transmission module 30 may be provided as a single module in which sub modules 31, 32, 33, and 34 for transmitting an image to a plurality of screens are integrated.

The image transmission module 30 may be controlled through a controller 20 of the headset 100. The controller 20 may control an activated image or a selected and activated image to be selectively transmitted to a specific screen.

The headset 100 may include an acceleration sensor 40 and a gyroscope 50. The acceleration sensor 40 and the gyroscope 50 may be provided to detect a change in the position of the head of the user. That is, a direction in which the eyes of the user gaze may be detected through a change in the position of the head of the user. In other words, whether the user stares at the main screen 12, the auxiliary screens 11 and 13, or the selection screens 21, 22, 23, and 24 may be detected.

A basic posture of the operating surgeon during surgery (i.e., the basic posture during endoscope surgery) may be different for each operating surgeon. The controller 20 may determine the position of the basic posture through the acceleration sensor 30 and the gyroscope 50. Needless to say, the positions of the basic posture may vary for each operating surgeon. This is because a comfortable posture during surgery may be different for each operating surgeon.

The controller 20 may control the main screen 12 to appear in front of the operating surgeon at the position of the basic posture.

The headset 100 may include an eye tracking module 60. The eye tracking module 60 may be a module that detects movement of the pupil of the user and tracks the position of the gaze. The headset 100 may include an infrared module for injecting infrared rays onto the cornea of the eye surface, and a camera module for recognizing infrared rays reflected from the cornea.

In particular, information on the position and time of a viewpoint may be recorded through the eye tracking module 60.

The eye tracking module 60 may detect a focus of the gaze of the operating surgeon by injecting infrared rays onto each of two pupils of the operating surgeon.

As described above, according to an embodiment of the present disclosure, information corresponding to a plurality of screens may be mapped. In particular, clarity of a surgical view during surgery is an important factor that affects treatment prognosis of the patient. Therefore, it is very important to place each screen at a position corresponding to a depth direction for providing optimal sharpness in consideration of a focal length of the operating surgeon. That is, the eye tracking module 60 may determine the focal length of the operating surgeon and arrange the screen at the optimal position.

For example, an inter-pupillary distance (IPD) and a pupil size, which are closely related to gaze focus in the depth direction, may be measured, and an optimal focal distance may be calculated based on these measurements. By providing a screen at the calculated focal length, the surgical view and the surgical assist function may be transmitted with optimal clarity.

Since the focal length differs depending on an operating surgeon of surgery, the arrangement position of screens in the virtual space may be different depending on the user. Through this function, it may be possible to provide a customized platform according to the user by automating focal length calculation of the user and screen arrangement position adjustment. In addition, the corresponding function may always be provided to reflect an IPD and a pupil size that change during surgery and to continuously optimize the position of the screen, thereby contributing to enhancing visual convenience of the user. This may ultimately have a positive impact on treatment prognosis of the patient.

The headset 100 may be operatively connected to peripheral devices. That is, the headset 100 may exchange data with peripheral devices and may include the input and output module 80 for this purpose. Through the input and output module 80, an endoscope image may be received, and an image and information of a necessary surgical assist function may be received. In addition, information selected and activated through the input and output module 80 may be requested and received by a peripheral device.

The headset 100 may include an artificial intelligence module 70. Needless to say, the artificial intelligence module 70 may be provided in a peripheral device other than the headset 100, particularly the main computer of the surgical robot system.

Through the artificial intelligence module 70, user fatigue may be predicted. For example, the gaze of the user may always be tracked through the eye tracking module 60, and a gaze path including time information of the gaze and information about a diameter of the pupil at that time may be recorded. As time elapses during surgery, concentration of the operating surgeon may decrease due to fatigue. A decrease in concentration of the operating surgeon may have a negative impact on prognosis of the patient, and thus rest may be recommended to restore fatigue and concentration. To this end, information such as time information of the gaze, a pupil diameter, and a gaze path, obtained using eye tracking technology, may be analyzed for a gaze pattern and an eye blink frequency using an artificial intelligence algorithm to quantify fatigue, and then, when the quantified fatigue exceeds a certain level, a rest recommendation function may be provided. This function may ultimately have a positive impact on the treatment prognosis of the patient through constant monitoring and improvement of the condition of the user (operating surgeon).

An image may be processed through the artificial intelligence module 70. In other words, surgery images may be processed in various forms by applying artificial intelligence-based image processing technology. Various surgical assist functions may be implemented through such image processing, which will be described below in detail.

Hereinafter, a type of a surgical assist function applicable to an embodiment of the present disclosure will be described in detail.

Since the vision device of the existing surgical robot only checks real-time surgical view during surgery, in order to check medical information about the patient, such as vital signs, the user needs to get out of a field of view limited to the vision device and check the corresponding information from the outside of the vision device. This has a limitation in that a flow of surgery is temporarily interrupted. Therefore, according to the present embodiment, the medical information of the patient, which is to be referred to during surgery, may be transmitted in real time to overcome the corresponding limitation using a surgical assist function. There may be CT, MRI, vital sign, electronic medical record (EMR), etc. as the medical information of the patient, which is to be provided, and medical information to be used according to a surgical area and type may be transmitted according to intention of the operating surgeon, thereby contributing to improving clinical convenience during surgery. That is, according to an embodiment of the present disclosure, the surgical assist function may include medical information of various patients.

When performing conventional traditional open surgery rather than robot surgery, the operating surgeon uses not only sight but also touch. However, the conventional robot surgery has a limitation that tactile sense of the operating surgeon is limited. In order to overcome this limitation, according to an embodiment of the present disclosure, visibility of a surgery scene may be improved by providing rich visual information to the operating surgeon during robot surgery. This contributes to improvement in clinical convenience for operating surgeons and positive prognosis of patients compared to conventional robot surgery.

The corresponding functions may be implemented using artificial intelligence-based image processing technology, and may provide hemorrhage highlighting and inter-tissue boundary display functions.

Figure 5:
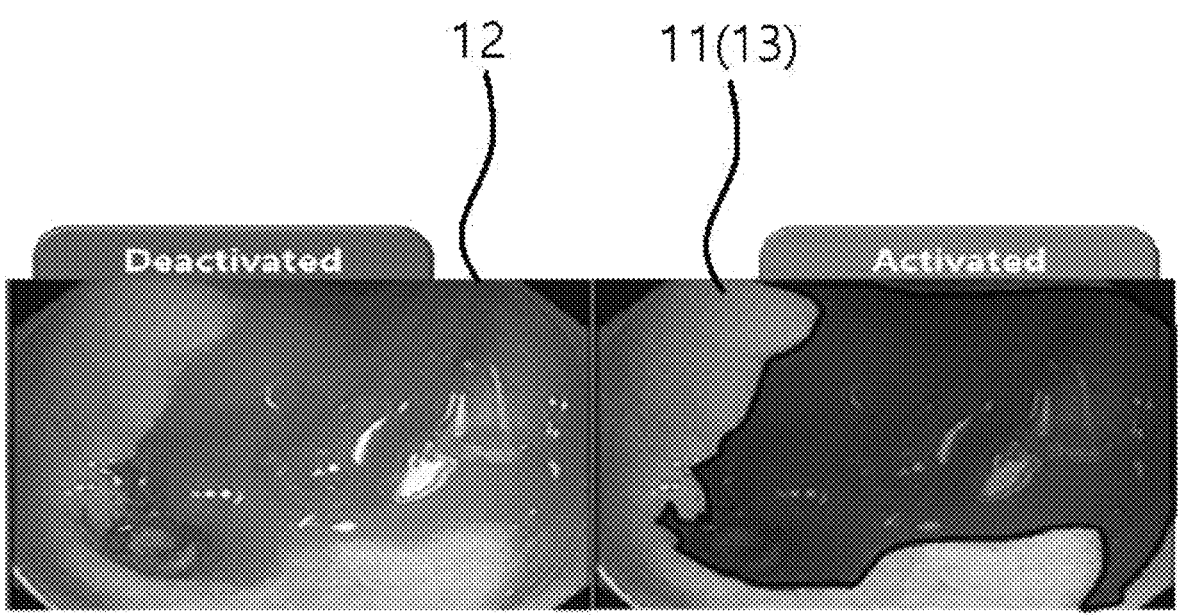
FIG. 5 shows an example of a hemorrhage highlighting function as a surgical assist function displayed on an auxiliary screen.

FIG. 5 shows an example of a hemorrhage highlighting function as a surgical assist function.

The image in which the hemorrhage highlighting function is deactivated may be the current endoscope image and may be transmitted to the main screen 12. The image with the hemorrhage highlighting function activated may be an image in which a hemorrhage part is emphasized by processing the current endoscope image based on artificial intelligence. The hemorrhage highlighting function may contribute to minimizing blood loss and ensuring a surgical view by intuitively highlighting a bleeding area. An image with the hemorrhage highlighting function activated may be transmitted on the auxiliary screens 11 and 13.

Figure 6:
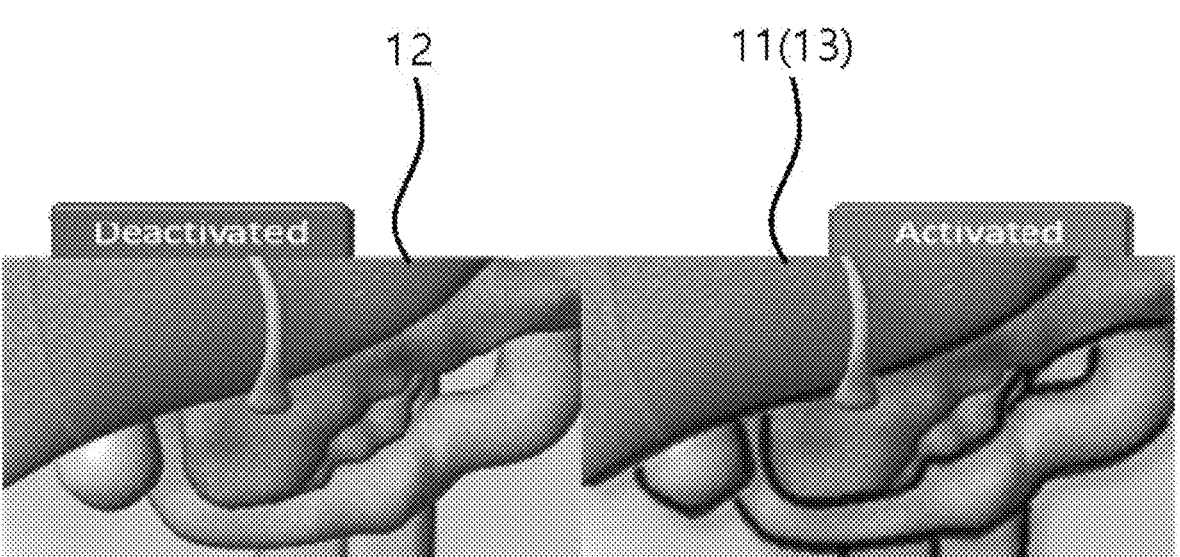
FIG. 6 shows an example of an inter-tissue boundary display function as a surgical assist function.

FIG. 6 shows an inter-tissue boundary display function as a surgical assist function.

A position prediction and visualization function of tissues (vessels and lesions) to be carefully treated according to an area in which surgery is performed may be provided. For example, when performing surgery on the thyroid gland, it may be necessary to perform surgery paying attention to nerves on both sides of the respiratory tract.

An image in which the inter-tissue boundary display function is deactivated may be the current endoscope image and may be transmitted to the main screen 12. The image in which the inter-tissue boundary display function is activated may provide a nerve position prediction and visualization function by processing the current endoscope image based on artificial intelligence. Through this, clinical convenience of the operating surgeon may be increased. Needless to say, an image in which the inter-tissue boundary display function is activated may be transmitted on the auxiliary screens 11 and 13.

That is, according to an embodiment of the present disclosure, the surgical assist function may include a visualization function for emphasizing a bleeding area, and major lesions and tissues in a surgical view.

Figure 7:
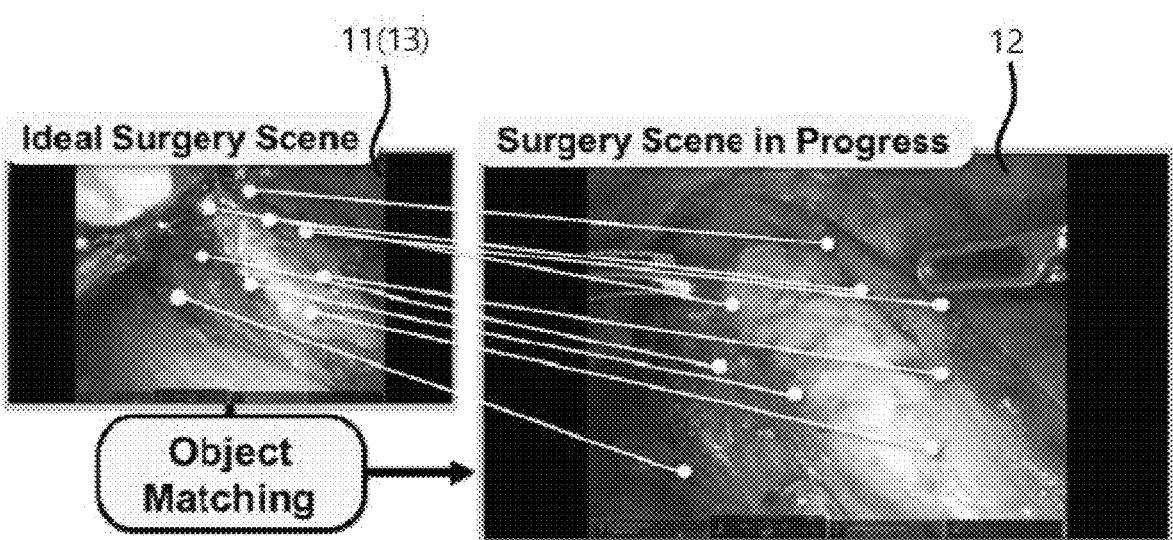
FIG. 7 shows an example of an ideal surgery scenario function as a surgical assist function.

FIG. 7 shows an ideal surgery scenario function as a surgical assist function.

During general surgery, there are differences in the detailed positions of lesions and surgical sites depending on the patient, but there are many cases in which a general framework of surgery does not change. Therefore, in a surgery stage in which there is a relatively high risk or precautions depending on the surgery being performed, the surgery process and scenes of the surgery case in which the corresponding stage is ideally completed may be provided to provide a guidance function for successfully performing a corresponding stage by the operating surgeon.

The corresponding function may be implemented using an image processing algorithm which detects feature points of an image, extracts the detected feature points feature information, and performs object matching according to the position of the feature points between images, such as scale invariant feature transform (SIFT) or speeded up robust feature (SURF). It may be possible to provide an ideal surgery scenario by designating specific lesions and tissues according to ongoing surgery as objects and comparing objects between surgical scenes.

The surgical view in progress may be an image transmitted on the main screen 12. In addition, an ideal surgery image that matches the ongoing surgical view may be an image transmitted to the auxiliary screens 11 and 13.

As the surgery stage progresses, the ideal surgery image in the corresponding stage may be continuously matched and transmitted to the auxiliary screens 11 and 13. Therefore, the operating surgeon may perform the current surgery with reference to the most ideal surgery image in the current surgery stage while performing the corresponding surgery stage.

Furthermore, when the surgery stage is performed, the overall flow of the provided ideal surgery may be analyzed, and when the operating surgeon applies gestures such as incision, suture, and hemostasis to lesions and tissues, the prognosis of the patient may be predicted and may be visually provided in real time.

Figure 8:
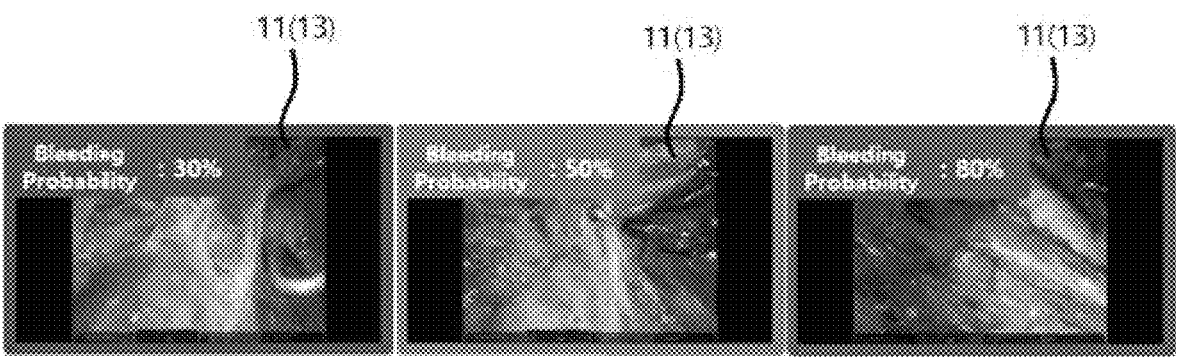
FIG. 8 shows an example in which a bleeding probability is calculated and displayed as an example of a prognostic prediction function as a surgical assist function.

FIG. 8 shows an example in which a bleeding probability is calculated and displayed as an example of a prognostic prediction function as a surgical assist function.

The prognostic prediction function may be a surgical assist function that goes beyond ideal surgery scenario analysis, enables prognostic prediction of the patient in the current surgery state and visualizes the prognostic prediction. For example, the prognostic prediction may be matched with the current surgery condition provided through the main screen 12 to predict a percentage of a bleeding probability, and the predicted image or video may be provided through the auxiliary screens 11 and 13. Needless to say, for the predicted prognosis of the patient, the bleeding probability may be calculated and displayed based on artificial intelligence algorithms.

In detail, in FIG. 8, colors of a background or an edge of an image may vary depending on the bleeding probability. For example, it may be possible to display green color when the bleeding probability is low, yellow color when the bleeding probability is normal, and red color when the bleeding probability is high. That is, parts of the image may be visually distinguished.

The operating surgeon may check that the auxiliary screens 11 and 13 show information that the bleeding probability is predicted to be 30% in green color, and know that the surgery is currently performed well, but the operating surgeon may check that the bleeding probability is predicted to be 80% in red color, and modify the surgery to increase a surgery success rate. Through this, the success rate may be increased. That is, according to one embodiment of the present disclosure, the surgical assist function may include a surgery guide and a prognostic prediction function.

Depending on a type of surgery, the surgery of the patient may not end one after another, and in this case, resurgery may proceed. In this case, a recorded primary surgery process may be provided to assist visually in resurgery. In other words, it may be possible to expect an effect of efficiently performing surgery on important points of an affected area on which the surgery is to be performed with reference to the primary surgery process.

A function for quantitatively calculating an improvement degree in the state of the affected area may be provided through comparative analysis between an image of an affected area at a time of completion of primary surgery and an image of the affected area at a time of resurgery based on an artificial intelligence algorithm, thereby contributing to determining whether the primary surgery is successful and establishing the direction of the resurgery. In addition, it may be possible to predict a time when the affected area is cured using information about a difference between two periods of the primary surgery and the resurgery and information about an improvement degree of the affected area. The predicted time may be expected to be used to establish a treatment plan of the patient in the future. That is, according to an embodiment of the present disclosure, the surgical assist function may include a function of calculating an improvement degree of the patient and a prognostic prediction function during resurgery.

Hereinafter, with reference to FIGS. 3 and 4, a method of activating and selecting a surgical assist function will be described in detail.

Figure 3:
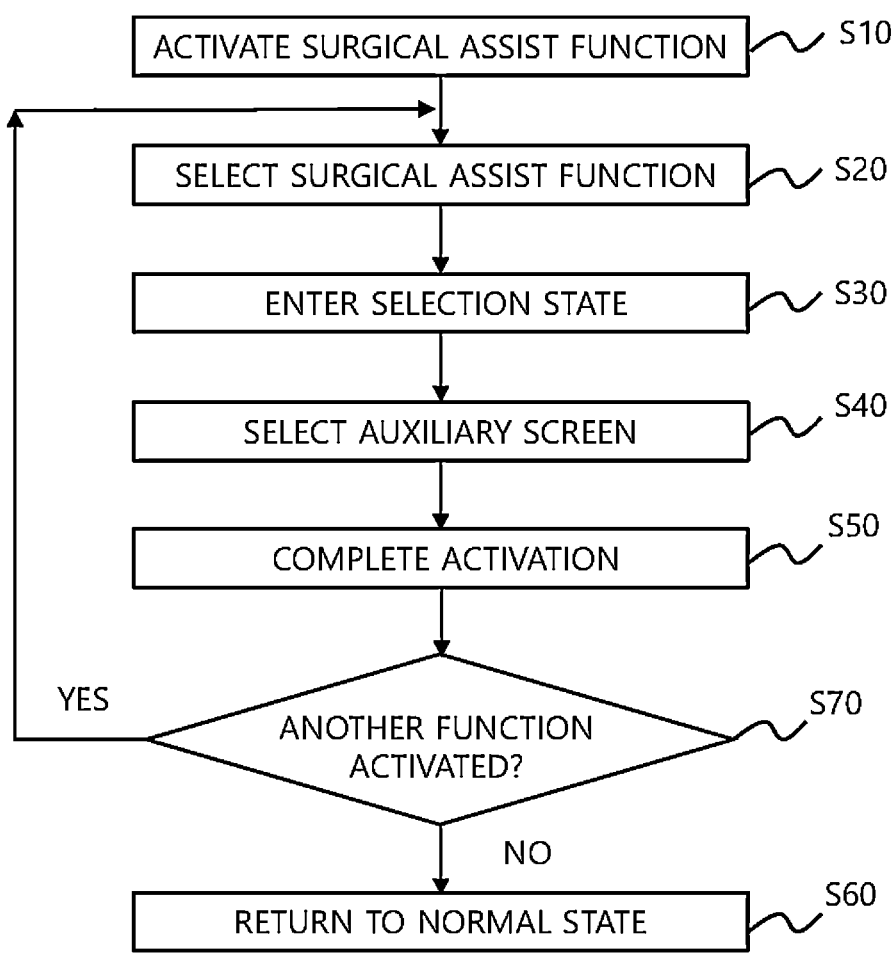
FIG. 3 is a flowchart showing activation of a surgical assist function and a auxiliary screen.
Figure 4:
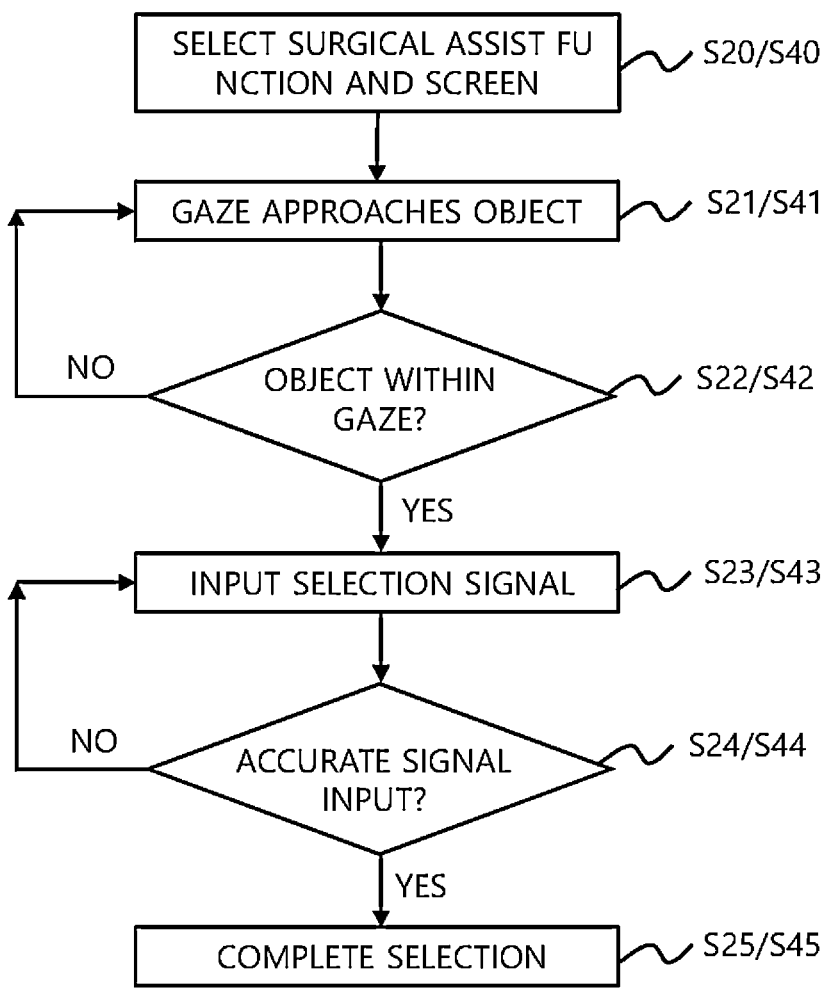
FIG. 4 is a flowchart showing a surgical assist function and auxiliary screen selection.

FIG. 3 is a flowchart showing activation of a surgical assist function. FIG. 4 is a flowchart showing a surgical assist function and auxiliary screen selection.

While performing surgery, the operating surgeon may request auxiliary information other than auxiliary information currently transmitted on the auxiliary screens 11 and 13. Needless to say, currently, any auxiliary information may not be transmitted on the auxiliary screens 11 and 13, and in this case, the operating surgeon may also request specific auxiliary information. That is, the current state may enter a surgical assist function activation state from a normal state (S10).

In order to enter the surgical assist function activation state, the operating surgeon needs to turn the head and the gaze at the auxiliary display 20. That is, even if there is no other manipulation or input, the current state may enter the surgical assist function activation state through a change in the gaze of the operating surgeon.

In this case, entry into the surgical assist function activation state may be confirmed through the acceleration sensor 40 or the gyroscope 50, and entry into the surgical assist function activation state may also be performed through the eye tracking module 60. Needless to say, information identified through these elements may also be used.

The operating surgeon may select a specific surgical assist function from among a plurality of surgical assist functions provided by the auxiliary display 20 (S20). That is, the operating surgeon may select the specific surgical assist function by blinking while staring at the specific surgical assist function. The number of blinks may be 2 to 3 times.

Through the eye tracking module 60, it may be possible to easily recognize that the operating surgeon blinks. This is because when the operating surgeon blinks, it means that infrared rays are not temporarily reflected through the cornea of the operating surgeon or the amount of reflection is remarkably small. Therefore, whether or not the eye blinks and the number of blinks may be determined very easily through an algorithm.

As described above, the position at which the operating surgeon currently gazes may be detected using sensors such as the acceleration sensor 40 and the gyroscope 50. Needless to say, as described above, the eye tracking module 60 may be used to determine the position at which the operating surgeon currently gazes. The position at which the operating surgeon currently gazes may be more accurately determined by using the sensors and the eye tracking module 60 in combination.

When the specific surgical assist function is selected through the gaze position and eye blinking of the operating surgeon, the current state may enter a selection completion state (S30), and then an auxiliary screen to display the selected specific surgical assist function may be selected (S40). That is, the operating surgeon may turn the head to stare at the specific auxiliary screen after the specific surgical assist is selected. For example, the auxiliary screen may be selected by staring at the right auxiliary screen 13 and then blinking 2 or 3 times.

Then, the selected specific surgical assist function may be transmitted and displayed on the right auxiliary screen 13, thereby completing activation (S50).

The surgical assist function activation state may be repeatedly performed. That is, after the transmission of the surgical assist function is completed, the operating surgeon may, for example, transmit another surgical assist function on the left auxiliary screen 11. In this case, the operating surgeon may select the surgical assist function in the same way and select a screen on which the selected surgical assist function is transmitted. Needless to say, the current state may also return to a default state. That is, whether another function is activated may be checked (S70), and a process of selecting a new surgical assist function may be performed, or the current state may enter or return to the default state (S60).

A detailed flow of the surgical assist function and screen selection will be described in more detail through FIG. 4.

As described above, selection of the surgical assist function may be performed while the operating surgeon turns the head toward the auxiliary display 20. Needless to say, screen selection may be performed while the operating surgeon turns the head toward a desired auxiliary screen. That is, specific flows of selection of the surgical assist function (S20) and selection of the auxiliary screen (S40) may be the same.

In detail, the acceleration sensor 40 and the gyroscope 50 may be embedded in the headset 100. In addition, the eye tracking module 60 may be embedded in the headset 100.

Based on the case in which the face of the user horizontally faces the front, it may be possible to determine an angle at which the face of the user moves left and right and up and down through the acceleration sensor and the gyroscope. Therefore, it may be possible to determine whether there is a selection object at a position at which the user currently gazes. That is, it may be possible to determine which surgical assist function is provided as an object or which auxiliary screen is provided as an object.

That is, through the acceleration sensor and the gyroscope, it may be possible to determine whether there is an object within the gaze (S22/S44) by approaching (S21/S41) a surgical assist function or auxiliary screen where the gaze of the user is an object. Needless to say, these stages may also be performed through the eye tracking module 60, or may be performed by using a sensor and the eye tracking module 60 in combination.

When there is an object within the sight, whether there is selection for the object may be determined. Selection of the object may correspond to a predetermined number of eye blinks through the eye tracking module 60. That is, the user may input a selection signal through eye blinking (S23/S43), and confirm whether there is an accurate signal input (S24/S44). An accurate input of the signal may by, for example, blink a predetermined number of times within a predetermined time.

When it is determined that there is an accurate signal input, selection of the object may be completed (S25/S45), and the selected result may be performed. That is, the specific surgical assist function may be selected, and the selected specific surgical assist function may be provided on a specific auxiliary screen.

An embodiment of the present disclosure may provide a robot surgery system for efficiently utilizing a space for surgery, and a vision device thereof.

An embodiment of the present disclosure may provide a robot surgery system for performing surgery in a more improved environment by relieving constraints of the operating surgeon on the vision device, and a vision device thereof.

An embodiment of the present disclosure may provide a robot surgery system for minimizing interruption of a flow of surgery and improving clinical convenience by providing various surgical assist functions to the operating surgeon through a headset, and a vision device thereof.

An embodiment of the present disclosure may provide a robot surgery system for easily activating and selecting a surgical assist function through a change in the gaze of the operating surgeon as well as providing a surgical view and a surgery auxiliary image in a VR environment, and a vision device thereof.

An embodiment of the present disclosure may provide a robot surgery system for providing a customized surgery platform depending on an operating surgeon, and a vision device thereof.

An embodiment of the present disclosure may provide a vision platform and a vision device which are to be easily applied to the conventional robot surgery system.

An embodiment of the present disclosure may provide a control method of a vision device to be easily used by an operating surgeon.

What is claimed is:

1. A method of operating a headset of a surgical robot system, the method comprising:

displaying, by a controller, a main screen and a pair of selectable auxiliary screens in a main display region, the selectable auxiliary screens being spaced apart from the main screen, wherein the main screen is located between the selectable auxiliary screens, wherein the main screen is aligned with the selectable auxiliary screens in a horizontal direction, wherein the main screen and the selectable auxiliary screens are activated simultaneously;

displaying, by the controller, a plurality of selection screens in an auxiliary display region spaced apart from the main display region, wherein the selection screens are aligned in a vertical direction;

displaying, by an endoscope image transmission module, an endoscope image on the main screen in the main display region;

displaying, by a surgical assist function optional transmission module, a list of selectable assist functions on the selection screens in the auxiliary display region, respectively;

activating, by a user, a surgical assist function state by turning a head and gazing at the auxiliary display region;

selecting, by the user, a specific assist function from the list of selectable assist functions by blinking while gazing at a corresponding selection screen;

selecting, by the user, a desired auxiliary screen from the selectable auxiliary screens by blinking while gazing at the desired auxiliary screen; and displaying, by a surgical assist function transmission module, surgical auxiliary information associated with the selected assist function on the selected auxiliary screen.

2. The method of claim 1, wherein the pair of selectable auxiliary screens include a left auxiliary screen provided on a left side of the main screen and a right auxiliary screen provided on a right side of the main screen.

3. The method of claim 1, further comprising informing, by an alarm transmission module, the user of break recommendation.

4. The method of claim 1, wherein the surgical auxiliary information displayed on the selected auxiliary screen is one of real-time medical information of the patient, visual information of a bleeding area in a surgical view, visual information highlighting major lesions or tissues in the surgical view, reference information for a surgery guide, surgery prognostic prediction information, or information on calculation of an improvement degree and prognostic prediction of the patient during resurgery.

5. The method of claim 1, further comprising transmitting and receiving, by an input and output module, data to and from a peripheral device of the surgical robot system.

6. A headset for a surgical robot system, the headset comprising:

a controller configured to display a main screen and a pair of selectable auxiliary screens in a main display region and to display a plurality of selection screens in an auxiliary display region spaced apart from the main display region, the selectable auxiliary screens being spaced apart from the main screen, wherein the main screen is located between the selectable auxiliary screens, wherein the main screen is aligned with the selectable auxiliary screens in a horizontal direction, wherein the main screen and the selectable auxiliary screens are activated simultaneously, wherein the selection screens are aligned in a vertical direction;

an endoscope image transmission module configured to display an endoscope image on the main screen in the main display region;

a surgical assist function optional transmission module displaying a list of selectable assist functions on the selection screens in the auxiliary display region, respectively; and a surgical assist function transmission module, wherein the controller is further configured to:

activate a surgical assist function state when a user turns a head and gazes at the auxiliary display region;

select a specific assist function from the list of selectable assist functions when the user blinks while gazing at a corresponding selection screen;

select a desired auxiliary screen from the selectable auxiliary screens when the user blinks while gazing at the desired auxiliary screen; and send a control signal to the surgical assist function transmission module to display surgical auxiliary information associated with the selected assist function on the selected auxiliary screen.

7. The headset of claim 6, wherein the pair of selectable auxiliary screens include a left auxiliary screen provided on a left side of the main screen and a right auxiliary screen provided on a right side of the main screen.

8. The headset of claim 6, further comprising an alarm transmission module configured to inform the user of break recommendation.

9. The headset of claim 6, wherein the surgical auxiliary information displayed on the selected auxiliary screen is one of real-time medical information of the patient, visual information of a bleeding area in a surgical view, visual information highlighting major lesions or tissues in the surgical view, reference information for a surgery guide, surgery prognostic prediction information, or information on calculation of an improvement degree and prognostic prediction of the patient during resurgery.

10. The headset of claim 6, further comprising an input and output module configured to transmit and receive data to and from a peripheral device of the surgical robot system.

* * * * *